(12) United States Patent
Castor

(10) Patent No.: US 11,234,932 B2
(45) Date of Patent: *Feb. 1, 2022

(54) COMBINATION HIV THERAPEUTIC

(71) Applicant: Trevor Percival Castor, Arlington, MA (US)

(72) Inventor: Trevor Percival Castor, Arlington, MA (US)

(73) Assignee: APHIOS CORPORATION, Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/698,382

(22) Filed: Nov. 27, 2019

(65) Prior Publication Data

US 2020/0093742 A1    Mar. 26, 2020

Related U.S. Application Data

(62) Division of application No. 15/576,190, filed on Nov. 21, 2017, now Pat. No. 10,493,030.

(51) Int. Cl.
| | | |
|---|---|---|
| *A61K 9/127* | (2006.01) | |
| *A61K 31/365* | (2006.01) | |
| *A61P 31/12* | (2006.01) | |
| *A61K 31/4045* | (2006.01) | |
| *A61K 31/19* | (2006.01) | |
| *A61K 31/325* | (2006.01) | |
| *A61K 31/167* | (2006.01) | |
| *A61K 31/20* | (2006.01) | |
| *A61K 47/69* | (2017.01) | |
| *A61K 47/68* | (2017.01) | |
| *A61K 38/15* | (2006.01) | |

(52) U.S. Cl.
CPC .......... *A61K 9/1271* (2013.01); *A61K 31/167* (2013.01); *A61K 31/19* (2013.01); *A61K 31/20* (2013.01); *A61K 31/325* (2013.01); *A61K 31/365* (2013.01); *A61K 31/4045* (2013.01); *A61K 38/15* (2013.01); *A61K 47/6851* (2017.08); *A61K 47/6913* (2017.08); *A61P 31/12* (2018.01); *Y10S 977/773* (2013.01); *Y10S 977/906* (2013.01); *Y10S 977/907* (2013.01)

(58) Field of Classification Search
CPC .............................. A61K 9/1271; A61K 9/127
See application file for complete search history.

(56) References Cited

U.S. PATENT DOCUMENTS

| 10,493,030 B2 * | 12/2019 | Castor ................ A61K 47/6913 |
| 2010/0166806 A1 * | 7/2010 | Castor ..................... A61P 31/18 424/400 |
| 2010/0247620 A1 * | 9/2010 | Castor ................ A61K 31/4745 424/450 |

FOREIGN PATENT DOCUMENTS

WO    WO-2013165592 A1 *    11/2013    ............. A61K 31/19

OTHER PUBLICATIONS

Daniel C. Buehler et al. "Bioengineered Vaults: Self-Assembling Protein Shell-Lipophilic Core Nanoparticles for Drug Delivery." ACS Nano, vol. 8, No. 8, 2014, pp. 7723-7732. (Year: 2014).*

Bernard Zappoli. "Near-critical fluid hydrodynamics." C. R. Mecanique, vol. 331, (2003), pp. 713-726. (Year: 2003).*

(Continued)

*Primary Examiner* — Isaac Shomer

(57) ABSTRACT

Embodiments of the present invention are directed to particles having a Bryoid and a HDAC inhibitor for the treatment of latent viral disease.

15 Claims, 2 Drawing Sheets

(56) References Cited

OTHER PUBLICATIONS

Figure 1:
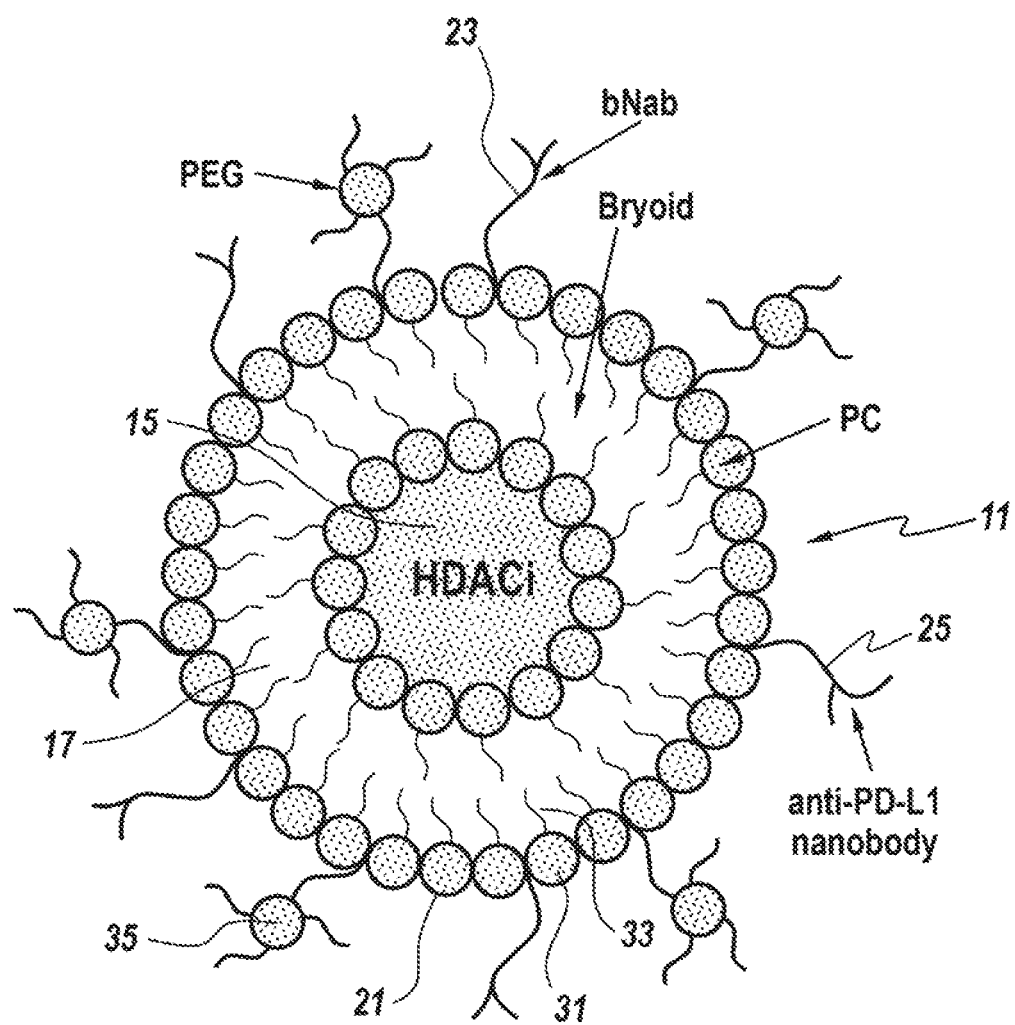

Michael Kovochich, Matthew D. Marsden, and Jerome A. Zack. "Activation of Latent HIV Using Drug-Loaded Nanoparticles." PLoS One, vol. 6 No. 4, Apr. 2011, e18270, pp. 1-8. (Year: 2011).*
AM Insogna et al.https://www.americanbar.org/groups/intellectual_property_law/publications/landslide/2012-13/september_october_2012/obviousness-type-double-patenting-who-would-have-thought-would-have-such-profound-effect-pharmaceutical-industry/ accessed Jan. 12, 2021, published 2012, pp. 1-13. (Year: 2012).*
Foley and Lardner. "Delayed Restriction Requirement Does Not Result in Patent Term Adjustment for Divisional Application." https://www.foley.com/en/insights/publications/2014/03/delayed-restriction-requirement-does-not-result-in accessed Jan. 12, 2021, published 2014, pp. 1-7. (Year: 2014).*

\* cited by examiner

Fig. 2

COMBINATION HIV THERAPEUTIC

RELATED APPLICATIONS

This application is a divisional of U.S. Ser. No. 15/576,190 filed Nov. 21, 2017, which claims priority to U.S. Provisional Application Ser. No. 62/165,444 filed May 22, 2015, which is incorporated by reference in its entirety herein.

STATEMENT REGARDING FEDERAL SPONSORSHIP

Embodiments of the present invention were not conceived nor reduced to practice with Federal funds or sponsorship.

FIELD OF THE INVENTION

Embodiments of the present invention relate to the field of latent viral diseases and articles of manufacture, compositions and methods for the treatment of such diseases.

BACKGROUND OF THE INVENTION

Antiretrovirus therapy (ART) is an indispensable life-saving therapy for millions of HIV+ individuals. However, the persistence of latent HIV-infected cellular reservoirs remains the last major hurdle to virus eradication. Latently infected cells represent a permanent source of potential viral reactivation. For this reason, the eradication of viral reservoirs is now the major goal for HIV-1 therapeutics (Richman et al., 2009).

SUMMARY OF THE INVENTION

Embodiments of the present invention are directed to medicaments, methods of treatment and articles of manufacture in the form of a particle for treating latent viral disease. As used herein, the term "medicament" broadly means any agent used in the treatment of a disease, such as, for example, without limitation, tablets, capsules, gelcaps, powders, patches, emulsion, suspensions and solutions which are administered orally, rectally, buccally, sublingually, subcutaneously, intramuscularly, intravenously and intraperitoneal.

One embodiment directed to a medicament comprises a Histone Deacetylase (HDAC) inhibitor, and a Bryoid, for treating a latent viral disease. One embodiment features a Bryoid is selected from the group of Bryostatins consisting of Bryostatin 1-20 and other known or identified Bryostatins. One embodiment features a HDAC inhibitor is selected from the group consisting of valproic acid, Vorinostat, Romidepsin and Panobinostat.

Embodiments of the present invention feature the administration of a Bryoid in a dose effective with the dose of the HDAC inhibitor. The Bryoid is administered in an effective dose range of 10 to 100 microgram/Kg subject every other day for up to 180 days.

Embodiments of the present invention feature the administration of HDAC inhibitor in a dose effective with the Bryoid. The HDAC inhibitor is administered in an effective dose range of 10 to 100 mg/Kg subject every other day for up to 180 days.

One embodiment of the invention features the HDAC inhibitor and Bryoid carried by one or more particles. As used herein, the term "carried by" refers to any configuration in which the HDAC inhibitor and Bryoid are associated with the particle. The term encompasses by way of example without limitation one or more of the HDAC inhibitor and Bryoid distributed throughout the particle, or on the surface of the particle or in a section of the particle.

One embodiment features one or more particles, in which the particle has a core, at least one surrounding material and an outer surface. The core has a mixture of a hydrophilic material and an HDAC inhibitor. The surrounding material has a mixture of a hydrophobic material and a Bryoid. The surrounding material envelopes the core and the outer surface surrounding the surrounding material. As used herein, the term "mixture" denotes a distribution whether in solution, in suspension or as an emulsion.

One embodiment of the invention features one or more particles for treating a latent viral disease having an outer surface. The virus associated with the latent viral disease has one or more viral components. The one or more particles comprise one or more ligands specific for the viral component and the one or more ligands associated with the outer surface of the one or more particles. For example, without limitation, the viral components comprise protein markers specific for Human Immunodeficiency Virus (HIV) and the particle surface comprises ligand such as antibodies, aptamers and similar constructs.

One embodiment of the invention features one or more particles which have one or more upregulating ligands to upregulate CD-4 cells. The one or more upregulating ligands are associated with the surface.

One embodiment directed to a method of treating a latent viral disease, comprises the step of administering an effective amount of a Histone Deacetylase (HDAC) inhibitor and an effective amount of a Bryoid. One embodiment of the method features a Bryoid selected from the group of Bryostatins consisting of Bryostatin 1-20 and other known or identified Bryostatins. One embodiment of the method features a HDAC inhibitor is selected from the group consisting of valproic acid, Vorinostat, Romidepsin and Panobinostat.

In one aspect of the method, the method Bryoid is administered in an effective dose range of 10 to 50 microgram/Kg subject. In one aspect of the method, the HDAC inhibitor is administered in an effective dose range of 10 to 100 mg/Kg subject.

One embodiment of the invention features the HDAC inhibitor and Bryoid carried by one or more particles. For example, without limitation one embodiment features a method wherein the one or more particles has a core, at least one surrounding material and an outer surface. The core has a mixture of a hydrophilic material and the HDAC inhibitor, and the surrounding material has a mixture of a hydrophobic material and the Bryoid. The surrounding material envelopes the core and the outer surface surrounds the surrounding material.

One embodiment of the method features the one or more particles having an outer surface and the virus associated with the latent viral disease having one or more viral components. The one or more particles comprise one or more ligands specific for the viral component, with the one or more ligands associated with the outer surface of the one or more particles.

One embodiment of the method features the one or more particles comprising one or more upregulating ligands to upregulate CD-4 cells. The one or more upregulating ligands are associated with the surface.

A further embodiment of the present invention is directed to an article of manufacture comprising a particle. The particle has a core, at least one surrounding material and an outer surface. The core has a mixture of a hydrophilic material and a Histone Deacetylase (HDAC) inhibitor. The surrounding material has a mixture of hydrophobic material and a Bryoid. The surrounding material envelopes the core and the outer surface surrounds the surrounding material. The particle is for treating a latent viral disease.

One embodiment of the invention features a particle wherein the virus associated with the latent viral disease has one or more viral components. The particle comprises one or more ligands specific for the viral component. The one or more ligands are associated with the outer surface of the particle.

One embodiment of the invention features a particle further comprising one or more upregulating ligands to upregulate CD-4 cells. The one or more upregulating ligands are associated with the outer surface.

One embodiment of the invention features a particle wherein the Bryoid is selected from the group of Bryostatins consisting of Bryostatin 1-20 and other known or identified Bryostatins. One embodiment features a particle wherein the HDAC inhibitor is selected from the group consisting of valproic acid, Vorinostat, Romidepsin and Panobinostat.

These and other features and advantages will be apparent to those skilled in the art upon viewing the drawings which are described in brief below and studying the Detailed Description of the Invention which follows.

BRIEF DESCRIPTION OF THE DRAWINGS

FIG. 1 depicts a cross sectional view of a particle embodying features of the present invention; and FIG. 2 depicts a schematic view of an apparatus for making the particle of the present invention.

DETAILED DESCRIPTION OF THE INVENTION

Different investigators have suggested that reactivation of the latent reservoirs with immunoactivation therapy would allow effective targeting and possible eradication of the virus. It is thought that viral reactivation by this therapy would result in lytic cell death of CD4+ T cells because of the cytopathic effect of the virus or through recognition of infected cells by the immune system. In addition, viral reactivation in the presence of ART would prevent new infections. In this sense a Histone Deacetylase (HDAC) inhibitor, Vorinostat, induced a significant and sustained increase in HIV transcription from latency in some HIV-infected patients but failed to clear HIV-1 reservoirs. These results indicate that additional strategies will be needed to eliminate latently infected cells.

Embodiments of the present invention feature Protein Kinase C (PKC) agonists such as the non-tumorigenic Bryoids combined with HDAC inhibitors to purge latent HIV-1 from cellular reservoirs. Currently, over 22 million people have died from AIDS and there are over 42 million people living with HIV/AIDS worldwide. In the United States, an estimated 1 million people are currently living with HIV and approximately 40,000 infections occur each year. There is no vaccine against HIV and AIDS, if untreated, will lead to the death of over 95% of infected individuals 10 years post-infection. HIV infects several cell types during the course of infection and progression to acquired immune deficiency syndrome (AIDS).

The persistence of latent HIV-infected cellular reservoirs represents the major hurdle to virus eradication with anti-retroviral therapy (ART), since latently infected cells remain a permanent source of viral reactivation. It has been hypothesized that intensification of ART could reduce the residual viremia but recent studies strongly suggest that this is not the likely scenario.

Moreover, ART is problematic because of long-term toxicity, inhibitor resistance, and the inability to target persistent reservoirs. Therefore, other pharmacological approaches targeting the HIV-1 reservoir have been suggested by several investigators as a promising strategy to develop new drugs able to activate latent HIV-1 without inducing a global T cell-activation.

HIV-1 infects several cell types during the course of infection and progression to AIDS. In the absence of ART, HIV-1 replication is active in most of the infected cells and in the majority of patients. However, HIV-1 establishes long-term infection in a small pool of memory CD4+ T cells and in other cell types, which contain integrated but transcriptionally silent HIV provirus. These latently infected cells constitute a viral reservoir in which a replication-competent form of the virus persists with more stable kinetics than the main pool of actively replicating virus.

Although ART is undoubtedly a life-saving therapy for millions of AIDS patients, the persistence of latent HIV-infected cellular reservoirs represents the major hurdle to virus eradication, since latently infected cells remain a permanent source of viral reactivation. As a result, a sudden rebound of the viral load after interruption of HAART is generally observed. For this reason, eradication of viral reservoirs is at present the major goal for HIV-1 therapeutics.

Early introduction and intensification of ART have been suggested to diminish the frequency of latently infected memory CD4+ T cells. However, a recent report has shown that ART intensification does not reduce residual viremia in a small cohort of patients. Moreover, it is believed that even a few, or a single, residually infected cell would be sufficient to produce systemic viremia upon ART interruption. Therefore, it has been hypothesized that reactivation of the latent reservoirs could allow effective targeting and possible eradication of the virus.

It is thought that viral reactivation would result in lytic cell death of CD4+ T cells because of the cytophatic effect of the virus or through recognition of infected cells by the immune system. In addition, viral reactivation in the presence of ART would also prevent new infection events. Developing drugs directed against different targets of the HIV cycle is urgently needed, especially the development of drugs able to diminish or eradicate latent reservoirs. This therapy should not induce polyclonal T cell activation.

The present invention features Protein Kinase C (PKC) agonists such as the non-tumorigenic Bryoids combined with Histone Deacetylase (HDAC) inhibitors to purge latent HIV-1 from cellular reservoirs. HDAC is an enzyme that removes acetyl groups from DNA bound histone proteins, affecting gene expression and contributing to HIV latency. Inhibitors of HDAC have been shown to reverse latency in vitro, ex vivo, and recently in a human clinical trial. Vorinostat, a HDAC inhibitor, failed to eliminate HIV-1 reservoirs in patients. Bryoids such as Bryostatin-1, as well as many PKC agonists, activates cellular transcription factors such as NF-κB that binds the HIV-1 promoter and regulates its transcriptional activity. In HIV-1 latency the viral promoter is less accessible to cellular transcription factors because nuclear histones surrounding the viral promoter are deacetylated (compacted chromatin). Thus, HDAC inhibitors may increase the acetylation of histones (relaxed chromatin) and then transcription factors may have an easier access to the HIV promoter.

One embodiment of the present invention features the administration of a Bryoid in a dose effective with the dose of the HDAC inhibitor. As used herein, the term "administer" or "administration" refers to the taking or receiving of a medicament in an effective manner, such as taking orally a tablet, capsule, powder, gelcap, liquid, suspension, emulsion or the like orally; or a liquid, emulsion or suspension for injection. The Bryoid is administered in an effective dose of 10 to 100 microgram/Kg subject every other day for up to 180 days.

One embodiment of the present invention features the administration of HDAC inhibitor in a dose effective with the Bryoid. The HDAC inhibitor is administered in an effective dose of 10 to 100 mg/Kg subject every other day for up to 180 days.

One embodiment of the invention features the HDAC inhibitor and Bryoid carried by one or more particles. Turning now to FIG. 1, a particle having features of the present invention, generally designated by the numeral 11, is depicted. The particle has a core 15, at least one surrounding material 17 and an outer surface 21. The core 15 has a mixture of a hydrophilic material and an HDAC inhibitor. The surrounding material 17 has a mixture of a hydrophobic material and a Bryoid. The surrounding material envelopes 17 the core 15 and the outer surface 21 surrounding the surrounding material 17.

The core 15 is an aqueous solution that forms a mixture with the HDAC inhibitor. The aqueous solution may comprise other constituents such as salts and buffering agents.

The surrounding material 17 is selected from hydrophobic compositions including phospholipids and like materials which form substantially uniform mixtures with a selected Bryoid. For example, without limitation, the phospholipid is selected from one or more of the group consisting of phosphatidylcholine (PC), phosphatidylglycerol (PG), phosphatidylserine (PS), dimyristoylphosphatidylcholine (DMPC), dimyristoylphosphatidylglycerol (DMPG), phosphatidylethanolamine (PE), and polyethylene glycol conjugated distearylphosphatidylethanolamine (either DSPE-PEG$_{2000}$ or DSPE-PEG$_{3500}$). Hydrophobic compositions include by way of example, without limitation α-tocopherol (vitamin E) and cholesterol. The phospholipids forming the hydrophobic material are depicted as a hydrophilic head 31 and a hydrophobic tail 33.

The virus associated with the latent viral disease has one or more viral components. For example, without limitation, the viral components comprise protein markers specific for Human Immunodeficiency Virus (HIV). As depicted, the outer surface 21 of the particle 11 comprises one or ligands 23 such as antibodies, nanobody, dual-variable domain ligands and similar constructs which bind to such protein markers. The antibody depicted is a broadly neutralizing antibody (bNAb).

As depicted, the particle has one or more upregulating ligands to upregulate CD-4 cells, an anti-PD-L1 antibody designated by the numeral 25. The one or more upregulating ligands are associated with the surface, similar to the ligand to the protein markers. That is, the head groups 31 of the phospholipids are modified to covalently carry a ligand.

As depicted, one or more head groups of one or more phospholipid compositions carry a polyethylene glycol modification 35. Polyethylene glycol modification of the phospholipid conveys decreased recognition by phagocytes.

Embodiments of the present invention feature targeting a combination of a Bryoid and an HDAC inhibitor co-encapsulated in a long-circulation pegylated immunonanosomes with coatings of broadly neutralizing antibodies and anti-PD-L1 nanobodies, as shown in FIG. 1, will provide efficient HIV latency activation and immunological depletion of latent reservoirs while significantly reducing systemic toxicities of both Bryostatin-1 and the HDAC inhibitor.

Using an in vitro model of HIV-1 latency, Jurkat-LAT-GFP, Bryostatin-1 re-activates HIV-1 latency in T cells via classical PKCs pathways. Bryostatin-1, at concentrations higher than 10 nM, induced translocation of cPKCs to the plasma membrane, and activated the canonical NF-κB and MAPKs (JNK and ERK) pathways.

In contrast, lower concentrations of Bryostatin-1 (10 nM) translocated cPKCs and Ras-GRP1 to the endoplasmic reticulum, activated ERK and the nuclear phosphorylation of p65 that fully reactivates HIV-1 latency. Low concentrations of Bryostatin-1 also down-regulated the expression of the human HIV-1 receptors CD4 and CXCR4 and prevent de novo HIV-1 infection (Perez, et al., 2010). Low concentrations of Bryostatin-1 activate the cPKC-Ras-Raf-ERK pathway and synergize with an HDAC inhibitor, vaiproic acid (VPA), to activate the transcription factor SP1.

Transcriptome studies found that low vs. high concentrations of Bryostatin-1 at 10 and 100 nM differentially regulate gene expression in T cells. Therefore, therapeutic activity can be achieved at concentrations that do not activate signal transduction pathways that may result in negative side effects.

Bryostatin-1 antagonized HIV-1 latency ex vivo in PBMC isolated from HIV-1 patients, and Bryostatin-1 at the doses of 10 and 20 μg/m2 did not induced significant adverse events in HIV-1 patients in a Phase I clinical study, Madrid, Spain (ClinicalTrials.gov NCT02269605).

In vitro studies suggest that very low concentrations of Bryostatin-1 (1-10 nM) synergizes with HDAC inhibitors such as valproic acid to antagonize HIV-1 latency (Perez et al., 2010). Thus, the therapeutic activity of Bryostatin-1 can be drastically improved in humans by utilizing a HDAC inhibitor. Our research indicates that combination therapy will be most effective, and reduce the therapeutic concentration of a Bryoid from 10 nM to 1 nM reducing systemic toxicities. Toxicities will be further reduced by encapsulating the combination therapeutic in liposomes which have been clinically shown to significantly reduce the in vivo toxicity of therapeutic drugs, e.g. the anti-fungal, amphotericin B.

The particle 11, as described, nanoencapsulates a non-tumorogenic Bryoid such as Bryostatin-1, which is quite hydrophobic in the lipid bilayer of a phospholipid nanosomes that are small, uniform liposomes, and co-encapsulate an HDAC inhibitor such as Romidepsin or Panobinostat in the aqueous core. Particles, of the type described in FIG. 1, are made in a process for the formation of small, uniform liposomes as described in U.S. Pat. No. 8,637,074 to Castor (2014).

Bryostatin-1 is encapsulated at concentrations of 1 to 100 nm with a preference of 1 to 10 nM and an HDAC inhibitor at concentrations of 30 to 1,000 nM with a preference of 30 to 100 nM. The utility of the co-encapsulation is that both drugs will reach their intended target at the same time, will be guided to the target with broadly neutralizing antibodies and the anti-PD-L1 nanobodies will keep CD4+ T-cells activated for clearing the activated HIV-1 virus. The immunonanosomes will further reduce systemic toxicities while pegylation will increase residence time of the circulating nanoparticle increasing therapeutic efficacy and overall therapeutic index.

Targeting a combination of a Bryoid and an HDAC inhibitor co-encapsulated in a long-circulation pegylated immunonanosomes with coatings of broadly neutralizing antibodies and anti-PD-L1 nanobodies, as shown in FIG. 1, will provide efficient HIV latency activation and immunological depletion of latent reservoirs while significantly reducing systemic toxicities of both Bryostatin-1 and the HDAC inhibitor.

Using an in vitro model of HIV-1 latency, Jurkat-LAT-GFP, we have shown that Bryostatin-1 re-activates HIV-1 latency in T cells via classical PKCs pathways. Bryostatin-1, at concentrations higher than 10 nM, induced translocation of cPKCs to the plasma membrane, and activated the canonical NF-κB and MAPKs (JNK and ERK) pathways.

In contrast, lower concentrations of Bryostatin-1 (10 nM) translocated cPKCs and Ras-GRP1 to the endoplasmic reticulum, activated ERK and the nuclear phosphorylation of p65 that fully reactivates HIV-1 latency. Low concentrations of Bryostatin-1 also down-regulated the expression of the human HIV-1 receptors CD4 and CXCR4 and prevent de novo HIV-1 infection (Perez, et al., 2010). We also found that low concentrations of Bryostatin-1 activate the cPKC-Ras-Raf-ERK pathway and synergize with an HDAC inhibitor, valproic acid (VPA), to activate the transcription factor SP1.

Transcriptome studies found that low vs. high concentrations of Bryostatin-1 at 10 and 100 nM differentially regulate gene expression in T cells. Therefore, therapeutic activity can be achieved at concentrations that do not activate signal transduction pathways that may result in negative side effects.

Bryostatin-1 antagonized HIV-1 latency ex vivo in PBMC isolated from HIV-1 patients, and Bryostatin-1 at the doses of 10 and 20 µg/m2 did not induced significant adverse events in HIV-1 patients in a Phase I clinical study, Madrid, Spain (ClinicalTrials.gov NCT02269605).

In vitro studies that very low concentrations of Bryostatin-1 (1-10 nM) synergizes with HDAC inhibitors such as valproic acid to antagonize HIV-1 latency (Perez et al., 2010). Thus, the therapeutic activity of Bryostatin-1 can be drastically improved in humans by utilizing a HDAC inhibitor. Our research indicates that combination therapy will be most effective, and reduce the therapeutic concentration of a Bryoid from 10 nM to 1 nM reducing systemic toxicities. Toxicities will be further reduced by encapsulating the combination therapeutic in liposomes which have been clinically shown to significantly reduce the in vivo toxicity of therapeutic drugs, e.g. the anti-fungal, amphotericin B.

To summarize the process of making the particle 11, of FIG. 1, in accordance with the teaching of Castor U.S. Pat. No. 8,637,074, reference is made to FIG. 2. Supercritical, critical or near-critical fluids with or without polar co-solvents at appropriate conditions of pressure and temperature are utilized to solvate phospholipids, cholesterol and other nanosomal raw materials. After a specific residence time, the resulting mixture is decompressed via a backpressure regulator (valve) though a dip tube with a nozzle into a decompression chamber that contains phosphate-buffered saline or other biocompatible solution. Bubbles will form at the injection nozzle tip because of SFS depressurization and phase-conversion into a gas, and the solvated phospholipids will deposit out at the phase boundary of the aqueous bubble. As the bubbles detach from the nozzle into the aqueous solution, they rupture, causing bilayers of phospholipids to peel off, thereby encapsulating solute molecules and spontaneously sealing themselves to form phospholipid nanosomes. Product volatilization and oxidation as well as processing time and organic solvent usage can be significantly reduced with the use of supercritical, critical or near critical fluids.

Figure 2:
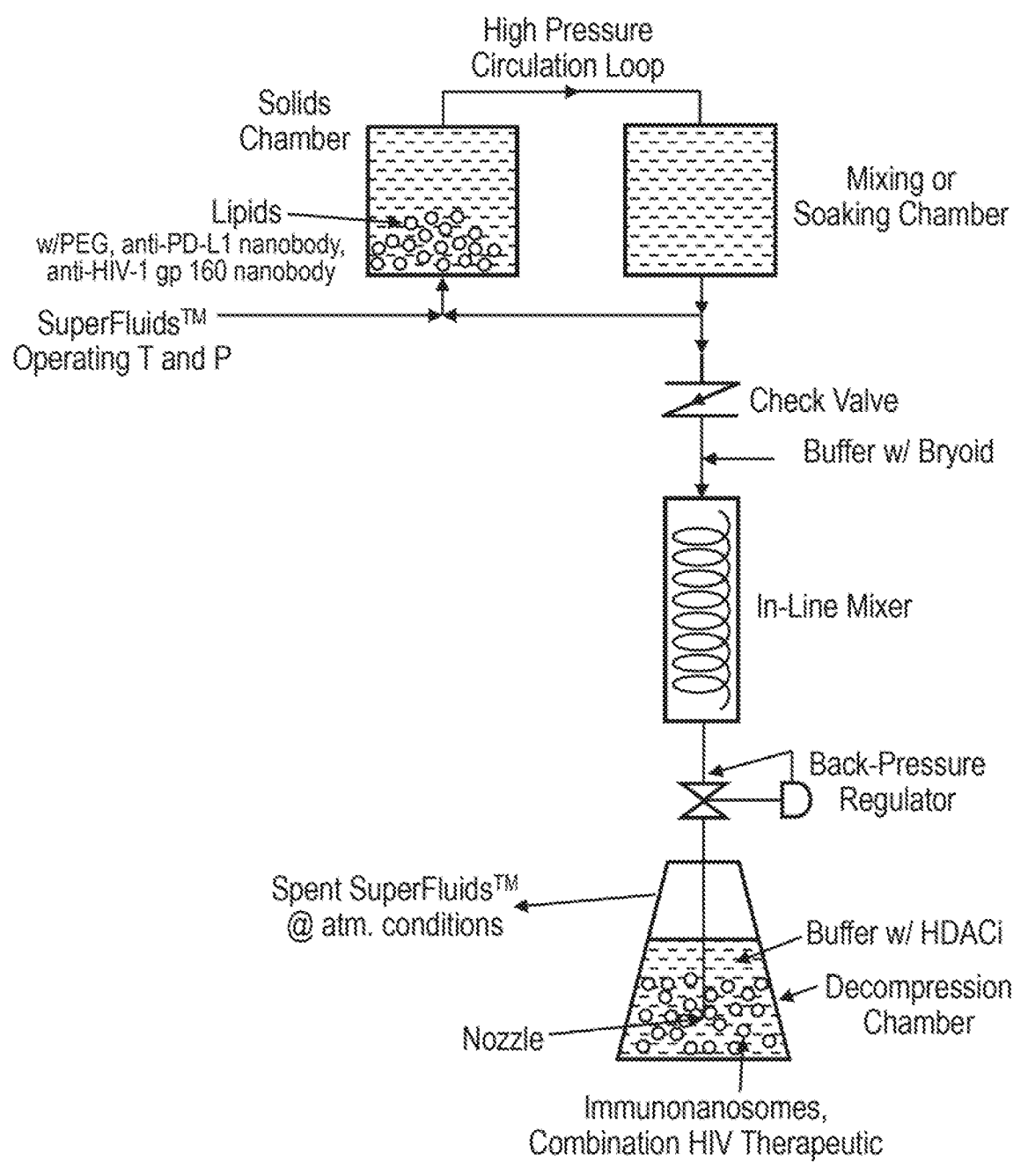

A Bryoid and HDAC inhibitor will be co-encapsulated in phospholipid immunonanosomes in the immunonanosomes apparatus shown in FIG. 2 with a supercritical, critical or near critical fluid such as carbon dioxide, nitrous oxide, fluorocarbon or alkane such as propane with or without a cosolvent such ethanol. A preferred supercritical, critical or near critical fluid is 80% propane and 20% ethanol at 3,000 psig and 40° C. We plan to use near-critical propane which, with a dipole moment of 0.084 Debyes, exhibits a much higher solvation power for phospholipids and hydrophobic drugs. Propane is considered GRAS (generally regarded as safe) by the FDA when used under GMP conditions in the food and pharmaceutical industries. Lipid materials will be selected on the basis of previous studies and the solubility of these lipids in the supercritical, critical or near critical fluid under appropriate operational conditions.

The presence of cholesterol in nanosomes transforms the bilayer into an ordered fluid phase over a wide temperature range, and therefore, improves the stability of nanosomes in plasma. Nanosomal compositions are listed in Table 1.

TABLE 1

Lipid Compositions and Molar Ratios

| Lipid Compositions | Molar Ratio |
| --- | --- |
| PC:CH | 1:1 and 2:1 |
| PC:PG:CH | 1:0.1:0.4 |
| PC:PS:CH | 1:0.1:0.4 |
| DMPC:DMPG:CH | 1:0.1:0.4 |
| PC:DMPG:CH:DSPE-PEG2000 | 1:0.1:0.35:0.05 |

The supercritical, critical or near critical fluid is utilized to first solvate phospholipids and liposomal raw materials, then mixed with a solution of the Bryoid prior to decompression and injection into a biocompatible solution containing the HDAC inhibitor. After decompression through a nozzle, the supercritical, critical or near critical fluid evaporates off, leaving an aqueous solution of liposomes entrapping hydrophobic Bryoid within the lipid bilayer and HDAC inhibitor in the aqueous core of the phospholipid nanosomes.

Phospholipids spliced with specific antibodies are utilized to target the co-encapsulated drugs to the latent HIV virus. The phospholipid nanosomes are coated with antibodies or nanobodies and are referred to as immunonanosomes by using phospholipids functionalized with the ligand.

One of the problems with nanosomes is phagocytosis by leukocytes and the reticuloendothelial system, which causes their rapid removal from circulation and makes them unavailable for uptake by tumor cells. This problem is overcome by coating the particles with polyethylene glycol (PEG) which prevents them from being recognized by phagocytic cells.

PEG coating is used to produce 'stealth' liposomes which make them non-recognizable by phagocytes and hence resistant to their uptake. Commercially available phospholipids with head groups linked to PEG of various molecular weights will be utilized. Pegylated phospholipids will be utilized to provide steric hindrance, increasing residence time and therapeutic index.

We also hypothesize that targeting a combination of a Bryoid and an HDAC inhibitor co-encapsulated in a long-circulation pegylated immunonanosomes with coatings of broadly neutralizing antibodies and anti-PD-L1 nanobodies, as shown in FIG. 1 will provide efficient HIV latency activation and immunological depletion of latent reservoirs while significantly reducing systemic toxicities of both Bryostatin-1 and the HDAC inhibitor.

Immunonanosomes are produced by various lipid materials in the size range of 100 to 200 (±50) nm. Immunonanosomal suspensions of this size range can be filtered by a 0.22 μm filter as a final sterilization step.

Particles, such as a plurality of particle 11, are used as a suspension in solution for administration by way of intravenous injection.

Thus, the present invention has been described in detail as an article of manufacture and a method of treating latent viral disease with the understanding that those skilled in the art can modify and alter the detailed description herein without departing from the teaching.

Therefore, the present invention should not be limited to the description but should encompass the subject matter of the claims that follow and their equivalents.

What is claimed is:

1. A method for making a nanosome for the treatment of latent viral diseases comprising forming an aqueous core having a mixture of a hydrophilic material and an HDAC inhibitor; forming a surrounding layer having a mixture of a phospholipid and a Bryoid; and forming an outer surface encapsulating said nanosome.

2. The method for making a nanosome for the treatment of latent viral diseases of claim 1, further comprising:

providing phospholipid material in supercritical, critical or near critical fluid;

providing a Bryoid in an alcohol solution;

forming a mixture of the phospholipid fluid and the Bryoid solution in an inline mixer;

decompressing the mixture using a backpressure regulator; and injecting said mixture as a stream through an injection nozzle into a decompression vessel containing an HDAC inhibitor in a hydrophilic aqueous solution.

3. The method for making a nanosome for the treatment of latent viral diseases of claim 1, further comprising coating the outer surface of the nanosome with antibodies effective in the treatment of said latent viral diseases.

4. The method for making a nanosome for the treatment of latent viral diseases of claim 3, wherein the viruses associated with said latent viral diseases include viral components, and wherein the method further comprises coating the outer surface of the nanosome with one or more ligands specific for the viral components of the viruses associated with said latent viral diseases.

5. The method for making a nanosome for the treatment of latent viral diseases of claim 4, wherein the one or more ligands on the outer surface of the nanosome upregulate CD-4 cells.

6. A method for making a nanosome for the treatment of latent viral diseases, said nanosome having an aqueous core having a mixture of a hydrophilic material and an HDAC (histone deacetylase) inhibitor, a surrounding layer having a mixture of a phospholipid and a Bryoid, and an outer surface;

Comprising:

providing phospholipid material in supercritical, critical or near critical fluid;

providing a Bryoid in an alcohol solution;

forming a mixture of the phospholipid fluid and the Bryoid solution in an inline mixer;

decompressing the mixture using a backpressure regulator; and injecting said mixture as a stream through an injection nozzle into a decompression vessel containing an HDAC inhibitor in a hydrophilic aqueous solution;

wherein bubbles form at the injection nozzle, detach from the nozzle, and rupture, causing bilayers of phospholipids to peel off, encapsulating solute molecules and spontaneously sealing to form a nanosome having a core of hydrophilic material and an HDAC inhibitor, a surrounding layer having a phospholipid and a Bryoid, and an outer surface encapsulating the nanosome.

7. The method for making nanosomes for the treatment of latent viral diseases of claim 6, wherein the hydrophilic aqueous solution in which the HDAC inhibitor is provided further comprises alcohol.

8. The method for making nanosomes for the treatment of latent viral diseases of claim 6, wherein the alcohol solution in which the Bryoid source is provided further comprises a buffer.

9. The method for making a nanosome for the treatment of latent viral diseases of claim 6, wherein the formed nanosome has a particle diameter between 100 nm and 200 nm.

10. The method for making a nanosome for the treatment of latent viral diseases of claim 6 wherein said Bryoid is a Bryostatin.

11. The method for making a nanosome for the treatment of latent viral diseases of claim 6, wherein said HDAC inhibitor is selected from the group consisting of valproic acid, Vorinostat, Romidepsin and Panobinostat.

12. The method for making nanosomes the treatment of latent viral diseases of claim 6, wherein phospholipid material is processed through a solids chamber, a mixing chamber, and a circulation loop for forming a phospholipid solution in a supercritical, critical or near critical fluid.

13. The method for making a nanosome for the treatment of latent viral diseases of claim 6, further comprising coating the outer surface of the nanosome with antibodies effective in the treatment of said latent viral diseases.

14. The method for making a nanosome for the treatment of latent viral diseases of claim 6, wherein the viruses associated with said latent viral diseases include viral components, and wherein the method further comprises coating the outer surface of the nanosome with one or more ligands specific for the viral components of the viruses associated with said latent viral diseases.

15. The method for making a nanosome for the treatment of latent viral diseases of claim 14, wherein the one or more ligands on the outer surface of the nanosome upregulate CD-4 cells.

* * * * *